United States Patent

Rembaum

[11] 4,013,507
[45] Mar. 22, 1977

[54] IONENE POLYMERS FOR SELECTIVELY INHIBITING THE VITRO GROWTH OF MALIGNANT CELLS

[75] Inventor: Alan Rembaum, Altadena, Calif.

[73] Assignee: California Institute of Technology, Pasadena, Calif.

[22] Filed: Feb. 5, 1975

[21] Appl. No.: 547,234

Related U.S. Application Data

[62] Division of Ser. No. 398,376, Sept. 18, 1973, abandoned.

[52] U.S. Cl. .......................... 195/1.8; 195/103.5 R
[51] Int. Cl.² ...................... C12B 1/00; C12H 1/04; C12K 9/00
[58] Field of Search ...................... 195/1.8, 103.5 R

[56] References Cited

OTHER PUBLICATIONS

Willmer – Cells & Tissues in Culture, vol. 3 (1966), pp. 360 & 361.

Primary Examiner—Sam Rosen
Attorney, Agent, or Firm—Marvin E. Jacobs

[57] ABSTRACT

Ionene polymers of the structure

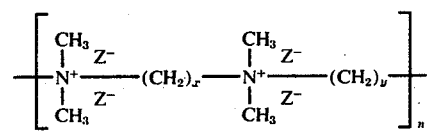

where $x$ and $y$ are integers from 3 to 16, $Z^-$ is an anion such as a halogen and n is an integer from 50 to 150 are found to bind negatively charged mammalian cells such as malignant cells and can be utilized to selectively inhibit the growth of malignant cells in vitro.

14 Claims, 4 Drawing Figures

IONENE POLYMERS FOR SELECTIVELY INHIBITING THE VITRO GROWTH OF MALIGNANT CELLS

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

CROSS REFERENCE TO RELATED APPLICATION

This is a division of application Ser. No. 398,376, filed Sept. 18, 1973, now abandoned.

BACKGROUND OF THE INVENTION

1. Field of the Invention

The present invention relates to biologically active polyquaternary polymers, and more particularly, to the use of ionene polymers to selectively bind negatively charged cells.

2. Description of the Prior Art

Early work with cell electrophoresis suggested that neoplastic, proliferating, and embryonal cells have a higher electro-negative surface charge than other types of cells. Each type of cell exhibits its own characteristic electronegativity, i.e. lymph node and spleen cells are more negative than thymocytes and macrophages. Cell membrane acid anions are the major cause of excess surface negative charge. More recently, a uniformity of electrokinetic pattern between normal and leukemic cells has been reported. The malignant cell lines HeLa (cervical cancer), HEp2 (laryngeal carcinoma), 256 (rat sarcoma), normal lymphocytes, and normal and malignant trophoblastic cells were found to have a common cell surface coating of an ionic nature not generally found for other normal cell types tested. Electron microscopic studies have also shown that malignant cells have an increased surface thickness of mucopolysaccaride material, containing terminal groups of negatively charged sialic acid moieties.

The use of polycations to cure or treat malignant cells is indicated by the electrostatic characteristic of the cell membrane. Polycation molecules may be monomeric or polymeric, of low or high molecular weight, may be linear or branched, and may have their charged quaternary group, (ammonium, sulfonium, or phosphonium), integral or pendant to the chain, with resulting biological properties extremely dependent upon these parameters. Many water soluble compounds are commercially available.

A difficulty in attempting to exploit electrostatic phenomenon in therapy of malignant disease stems from the lack of specificity for tumor cells by polycations and also the constantly changing surface chemistry of cell membranes. Nevertheless, the possibility of employing polycations for preferential growth inhibition of malignant cells has been attempted.

Several classes of polycations, primarily quaternary polyethylene imine (PEI), polypropylene imine (PPI), polyvinylimidazolinium (PVA), and diethyl amino ethyl dextran (DEAD) have been found to inhibit the growth of allogeneic and syngeneic tumors in mice at non-toxic levels to the host. Anti-tumor activity appears related to the polycation type, molecular weight, zeta potential and route of injection. While these agents are cytotoxic, only a few have been shown to exhibit any specificity for tumor cells, i.e. the capability of non-toxic action on normal cells while exhibiting toxic activity with respect to malignant cells. Furthermore, these commercial polymers are not well characterized as to structure and molecular weight and are of questionable purity.

Monomeric polyquaternary cations of aliphatic and heterocyclic structure such as ditertiary aliphatic diamines and bisquaternary pyridine compounds have been suggested for use as curariform and anti-tumor agents. The binding efficiency, toxicity and duration of activity have not been totally satisfactory.

SUMMARY OF THE INVENTION

In accordance with the invention, it has now been discovered that polycationic ionene polymers and especially particular ionene polymers under controlled dosage limits exhibit selectivity toward malignant mammalian cells when added to a mixture of normal and malignant cells. In animal tests, the ionene polymers demonstrated anti-tumor activity by partial rejection of transplanted tumors and increased survival time. In vitro test with a mixture of normal and malignant cells demonstrated growth of the normal cells while exhibiting toxic action toward the malignant cells. The ionene polymers are found to be safe and effective under conditions of usage.

These and other objects and attendant advantages of the invention will become better understood by a reference to the following detailed description when considered in conjunction with the accompanying drawings.

DESCRIPTION OF THE PREFERRED EMBODIMENTS

Figure 1:
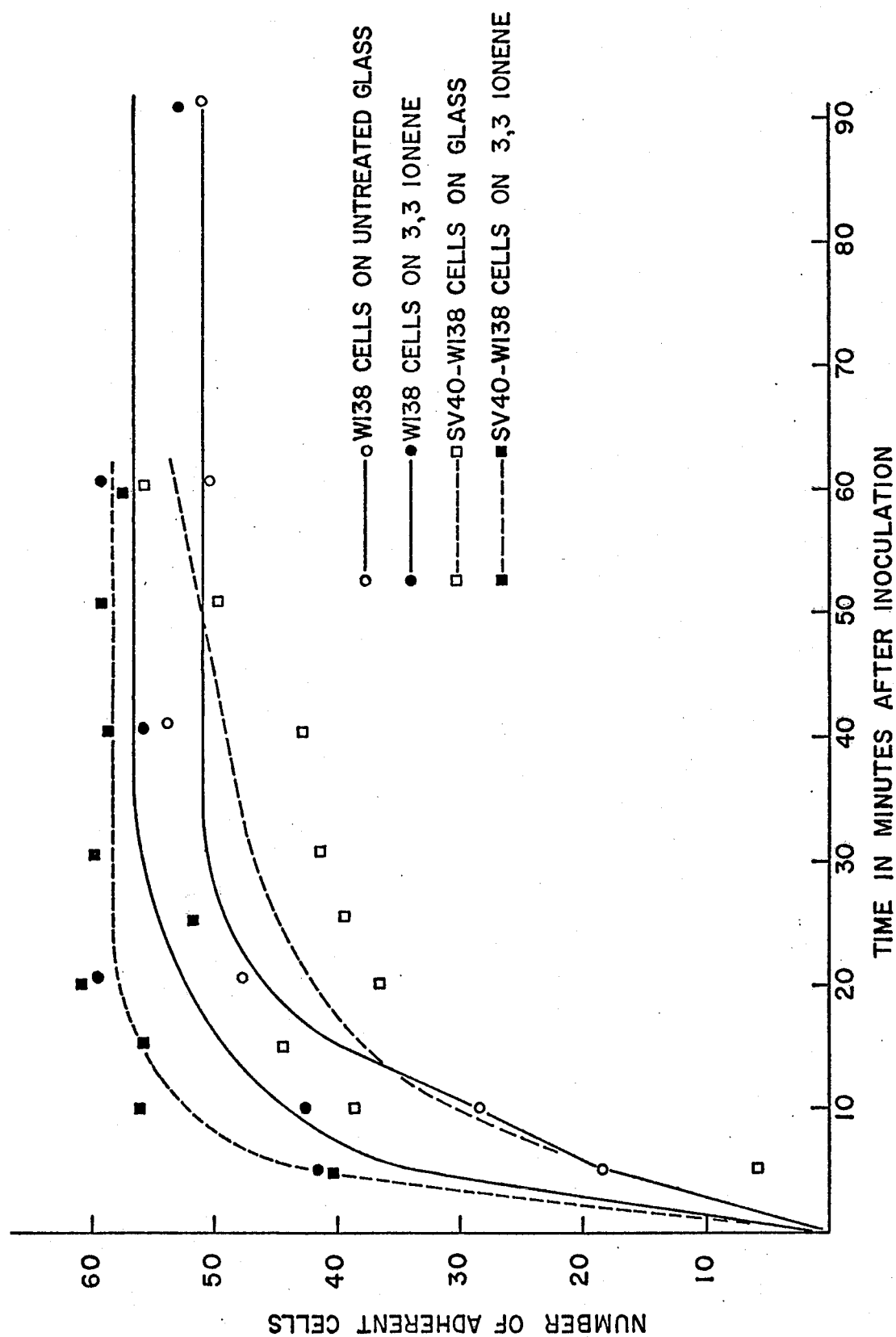
FIG. 1 is a series of curves showing the differential adhesion of cells to glass surfaces and to glass surfaces coated with 3,3-ionene.

The ionene polymers of interest in this invention are water-soluble, linear polymers, without cross-linking or branching. The polymers have a molecular weight from 3,000 to 100,000, generally from 10,000 to 60,000 and are solids at room temperature and have an average charge of at least one intra polymeric quaternary nitrogen for an average of every 12 chain atoms.

The ionenes have the general structure:

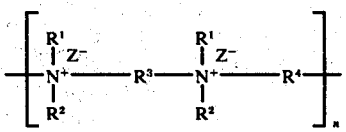

where $R^1$ and $R^2$ are methyl, $R^3$ and $R^4$ are divalent aliphatic, aromatic or heterocyclic groups containing at least 3 carbon atoms, or $R^3$ combined with $R^1$ and $R^2$ forms a cyclic group and $Z^-$ is an anion, generally chloro, bromo or iodo.

Aliphatic ionene polymers in which $R^3$ and $R^4$ are the same polymethylene group of the formula $(CH_2)_x$ where $x$ is 3 or more than 6 can be prepared by homopolymerization of tertiary amino alkyl halides of the formula

in accordance with the procedure disclosed in copending application Ser. No. 280,649, filed Aug. 14, 1972. Values of $x$ between 4 and 7 result in cyclic products.

Ionenes can also be prepared by the copolymerization of ditertiary amines and dihalo organic compounds. This reaction permits the synthesis of a variety of linear polymers in which the distance between positive nitrogen centers can be varied at will. With aliphatic ionenes of the formula:

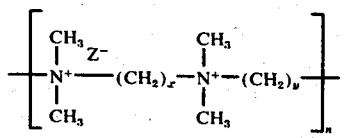

the values of $x$ and $y$ between 3 and 16 must also be selected to avoid formation of cyclic compounds, as disclosed by Rembaum et al. Macromolecules 5 261 (1972), the disclosure of which is incorporated herein by reference.

Well defined conditions of synthesis relating to formation of relatively high molecular weight ionenes are disclosed by Rembaum et al, J. Polym Sci., Part B 6 159 (1968), the disclosure of which is incorporated herein by reference. Generally, high molecular weight ionene polymers are prepared in a 0.1 to 2.5 molar solution of a ditertiary amine and a dihalo organic compound in solvent at temperatures below about 50° C. Higher polymerization rates occur in polar organic solvents such as dimethyl formamide (DMF), dimethyl sulfoxide (DMSO), methanol, preferably a mixture of DMF and methanol.

The dihalo organic material is a compound of the formula $ZR^4Z$ where Z is chloro, bromo or iodo, where $R^4$ is a divalent organic radical such as alkylene, arylene, alkarylene or aralkylene. Hydrocarbon $R^4$ groups may also be interrupted with atoms such as nitrogen, oxygen or sulfur and may be substituted with diverse pendant groups that do not interfere with the polymerization reaction or activity of the polymer or promote undesirable side effects during use.

Representative dihalo organic compounds are $\alpha,\delta$-chloro or bromo terminated compounds such as 1,3-dichloropropane, 1,3-dibromopropane, 1,4-dichlorobutane, 1,4-dibromobutane, 1,4-dichloro-2-butene, 1,4-dibromo-2-butene, 1,4-dibromo-2,3-dihydroxy butane, 1,5-dichloropentane, 1,6-dibromohexane, 1,8-dichlorohexane, 1,10-dichlorodecane, and 1,16-dichlorohexadecane. The alkenylene compounds are more reactive than the corresponding saturated compounds. Dihalo aromatic compounds such as o, m, and p-dichloro or -dibromo xylene may also be utilized. A compound of particular utility can be formed from a dihalo compound of known anti-tumor activity. For example, cyclophosphamide, commercially known as cytoxan, can be reacted with ditertiary amines to form biologically active polymers in accordance with the invention.

The diamine reactant for the copolymerization reaction may be represented by the formula:

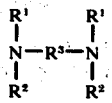

where $R^3$ is aliphatic, aromatic, heterocyclic or $R^3$ when combined with $R^1$ and $R^2$ forms a cyclic group. Representative compounds are N,N,N',N'-tetramethyl-1,3-diamino propane, N,N,N',N'-tetramethyl-1,3-hexamethylene diamine (THD) and N,N,N',N'-tetramethyl1,10-decamethylene diamine. Examples of heterocyclic or aromatic compounds are 1,2-bis-(4-pyridyl)-ethane, -propane or -butane, dipyridyl, diazo-bicyclooctane or tetramethyl diamino, diphenyl methane. The copolymerization synthesis of the invention is particularly adaptable to precursors of known anti-tumor agents such as the bis-pyridyl compound of the formula:

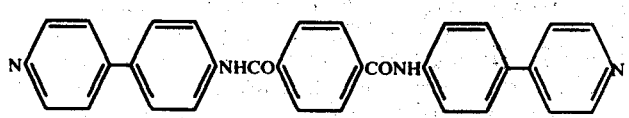

and the corresponding 3-phenyl pyridine isomer thereof which have been shown to be very effective against the L1210 leukemia system when quaternized (J. Med. Chem. 10, 706, 1967).

The invention will now be illustrated by the following examples.

EXAMPLE 1

Tetramethyl-3,4-Ionene Bromide

Tetramethyl-3,4-ionene bromide was produced under the following conditions: 6.26 g of N,N,N',N'-tetramethyl-1,3-diaminopropane and 10.4 g of 1,4-dibromobutane were dissolved in methanol, total volume 25 ml. The resulting solution was equilibrated at 25° C for 1 week. Immediately prior to isolating the product, an aliquot was analyzed for unquaternized amine, which was found to be 0.5% of the initial monomer. The solvent was flash evaporated, and the polymer dried under vacuum at 40° C for 24 hours. 16.7 g (88% yield) of 3-4,ionene bromide was isolated. Bromine analysis gave 42.6% ionic bromine compared to a theoretical value of 46.2%. The intrinsic viscosity of the polymer, as determined in 0.4 M KBr (aq), was [n] = 0.194 dl/g corresponding to a molecular weight of about 45,000.

EXAMPLE 2

3,4-Ionene Chloride

The chloride corresponding to the ionene polymer of Example 1 was prepared by substituting an equivalent amount of 1,4-dichlorobutane for the dibromobutane and following the procedure of Example 1.

EXAMPLE 3

6,10-Ionene Bromide

N,N,N',N-tetramethylhexamethylene diamine (THD), (one equivalent) is mixed with normal dibromodecane (one equivalent), each material having been previously dissolved in a 1:1 by volume mixture of dimethylformamide and methanol. The mixture was allowed to react at room temperature for a period of 1 to 10 days. At the end of this time, benzene was added to the mixture. The precipitated solid which formed was filtered, washed with benzene, and suitably dried. The yield was about 90–99% based on theoretical, of a white crystalline solid with a molecular weight of about 50,000. Spectral and elemental composition analysis showed the structure to be a linear polymer of the formula:

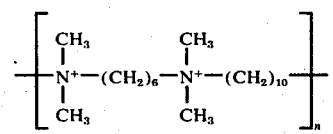

EXAMPLE 4

6,10-Ionene Chloride

The corresponding chloride was formed by substituting an equivalent amount of dichlorodecane for the dibromodecane and following the procedure of Example 3.

EXAMPLE 5

3,3-Ionene Bromide

A 1:1 molar solution of tetramethyl diaminopropane (0.2 mol) was thoroughly mixed with 1,3-dibromopropane (0.2 mol) in 1:1 DMF/methanol by volume. The mixture was left at room temperature (ca. 22° C) for 9 days. The polymer was filtered, washed quickly with a small amount of solvent, then with benzene and finally with acetone and dried under high vacuum at 40° C to yield a polymer having a molecular weight of about 55,000.

EXAMPLE 6

3,3-Ionene Chloride

The corresponding chloride was formed by substituting an equivalent amount of dichloropropane for dibromopropane and following the procedure of Example 5.

EXAMPLE 7

PC-6

Cyclophospamide and an equivalent amount of αω-tetramethyl amino-n-hexane were reacted in bulk at 50° C for 48 hours to form a new polymer which was named polycytoxan-6(PC-6), having a molecular weight of at least 10,000 and having the following structure:

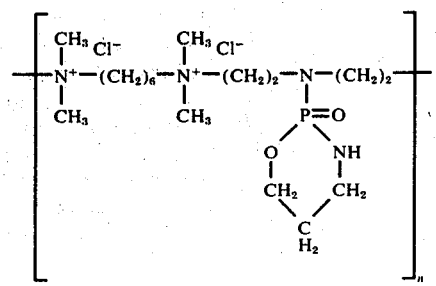

Based on an area of 100 $A^{o2}$ per molecule, the charge density of 3,4-ionene has been estimated at $9.6 \times 10^{-12}$ electrostatic units/$A^{o2}$ and for 6,6-ionene at $6.4 \times 10^{-12}$ esu/$A^{o2}$.

Due to the high positive charge density and high water solubility, ionenes strongly interact with a wide variety of cell materials. Ionene polymers exhibit toxic effects when injected into mice intraperitoneally (i.p.). The i.p. lethal dose for 50% survival (i.p. $LD_{50}$) is, however, comparable to that of a number of clinically used drugs. Oral administration of ionene polymers is considerably less toxic than intraperitoneal. A comparison of i.p. $LD_{50}$ with oral i.p. $LD_{50}$ is shown in the following Table in which the toxicity data for some low molecular weight ammonium salts are also included.

TABLE I

TOXICITY OF POLYMERIC VERSUS MONOMERIC COMPOUNDS

| | i.p. LD50 mg/kg | Oral LD50 mg/kg |
|---|---|---|
| 3,3-ionene bromide | 50–100 | 500–1000 |
| 2,4-ionene bromide | 50–100 | >1000 |
| 2,6-ionene bromide | 50–100 | >1000 |
| 6,3-ionene bromide | 50–100 | >1000 |
| 6,4-ionene bromide | 50–100 | >1000 |
| 6,5-ionene bromide | 50–100 | >1000 |
| 6,6-ionene bromide | 50–100 | >1000 |
| 6,10-ionene bromide | 10–50 | 500–1000 |
| 6,16-ionene bromide | 50–100 | >1000 |
| BrCH₂N⁺(CH₃)₂—(CH₂)₆—N⁺(CH₃)₂CH₂Br | 10–50 | 300–500 |
| Br—CH₂CH₂—N⁺(CH₃)₂—(CH₂)₆—N⁺(CH₃)₂CH₂CH₂Br | 10–50 | 100–200 |
| BrCH₂N⁺(CH₃)₂—(CH₂)₄—N⁺(CH₃)₂CH₂Br | >1000 | >1000 |
| (CH₃)₂N⁺ cyclic (pyrrolidinium) | 100–200 | >1000 |
| (CH₃)₂N⁺—N⁺(CH₃)₂ cyclic (piperazinium) | >1000 | >1000 |

The ionene polymers of this invention may be utilized to cure and treat traumatic conditions of warm blooded animals and particularly mammals such as dogs, cats and humans. The polymers will find use in clinical and veterinary medicine and as diagnostic agents and as agents useful in the study of biosynthesis mechanisms of growth of normal and abnormal cells. The polymers may be ingested orally or may be administered by subcutaneous, intermuscular or intraperitoneal routes.

The ionene polymers are suitably dispersed or dissolved in a pharmacologically acceptable carrier such as aqueous phosphate buffer at a pH of about 7 or more. The polymers may also be compounded with inert adjuvants or excipients such as flavoring agents, coloring agents and fillers and extenders to package the ionene polymer in a unit dosage form. The polymer may be administered on a regular daily basis since it has shown sustained, long-term activity or may be administered in smaller dosages several times a day on a scheduled basis as indicated by the condition of the subject. Minimum daily dosage depends on the weight of the animal, the condition being treated and the route of administration. The dosage level by oral route must be maintained below about 500–1000 mg/kg and below 50–100 mg/kg by the i.p. route. Animal experiments have indicated that a daily dosage level of at least 1 mg/kg and preferably 5–25 mg/kg administered intraperitoneally is safe and effective in the treatment of animals with malignant tumors. Daily oral dosages of 50 to 200 mg/kg would also appear to be safe and effective.

Ionene polymers may be utilized in combination with other pharmacologically active compounds of similar or complementary activity. Ionene polymer therapy may be combined with other polycations such as polyethylene imine or with heparin.

Ionenes form water insoluble complexes with heparin. The solubility of these complexes depend on the structure of ionene and the molecular weights of both components. Complex formation is probably the reason for the antiheparin activity of ionenes.

Protamine sulfate and toluidine blue, neither of which are free of toxic effects, are clinically used as antiheparin agents. Although most ionene structures have antiheparin activity, extensive investigations of toxicology and effects on the circulatory system in laboratory animals were carried out with 6,3-ionene bromide. The latter was found to be more toxic (the i.v. $LD_{50}$ being 28 mg/kg in mice and 20 mg/kg in rats; the i.p. $LD_{50}$ in mice being 61.5 mg/kg) than toluidine blue (i.v. $LD_{50}$ 45 mg/kg) and protamine sulfate (i.v. $LD_{50}$ 44 mg/kg). However, cumulative i.v. doses of 6,3-ionene bromide up to 5 mg/kg as 1% solutions could be given rapidly to anesthetize dogs without markedly affecting either the respiration or circulation, i.e., without toxic symptoms.

Heparin offers a protective action in neutralizing the toxicity of 6,3-ionene bromide in both mice and dogs. Thus pretreatment of mice with heparin enabled them to survive doses three times the $LD_{50}$ values with only mild toxicity symptoms. This is not surprising considering the formation of relatively stable complexes between ionenes and heparin.

The nature of binding of ionene polymers and the resultant biological activity against normal and cancerous cells was tested by in vitro growth experiments. The host cells were normal epithelial human lung cells (WI-38) and SV-40 transformed WI-38 cells. Due to the high positive charge density and high water solubility, the ionenes strongly interact with a wide variety of biological materials. Since it has been suggested that malignant cells are more electro-negative than normal cells, malignant cells should demonstrate a greater affinity for the electro-positive ionene polymer. A series of studies were carried out to evaluate the degree of cellular adherence and spreading capacity of normal and SV-40 transformed human cells (WI-38) on normal glass surfaces and on glass which was coated with ionene. In the study, mammalian cells were in culture with ionenes as molecular probes to understand the cell membrane properties. The surface of most mammalian and avian cells has a net negative charge. Several altered cell membrane characteristics are most noticeable in transformed cells. This results in an impairment of the social interactions evolving at cell surfaces, inherent in malignancy. With some exceptions, the net surface negativity increases by about 20% in a transformed cell. This difference in the surface charge results in the differential cell-cell aggregation and also in differential cell-substratum adhesion, since the substratum-like glass also has a net negative charge.

Using normal human diploid fibroblast cells WI-38 and its SV-40 transformed derivative WI-38 VA132RA (SV-40-WI-38), a series of experiments were conducted with 3,3-ionene bromide and 6,10-ionene bromide on the cell adhesion, and cell spreading on glass surfaces coated with ionenes. Preliminary studies on differential toxicity to normal and transformed cells were also conducted.

The polycation-coated glass surface would shift the surface charge in favor of positivity, accelerating the cellular adhesion. Since the transformed cells have about 20% more negative charge than the normal ancestors, the transformed cells may adhere and spread faster than the normal cells to polycation-coated glass surfaces. WI-38 cells of passage 17-22 and SV-40-WI-38 cells of passage 194-206 were utilized in these experiments.

Adhesion of cells was routinely measured in multiplate (Lux Scient. Corp.) in which Gold seal coverglasses were used as substratum for cell adhesion. Two of the coverglasses were soaked for 30 minutes in 3,3-ionene Br solution (2μg/ml) in $Ca^{++}$ and $Mg^{++}$ free Hanks solution, rinsed twice with $Ca^{++}$ and $Mg^{++}$ free Hanks solution (pH 7), while the other two served as controls.

Three 4 day old cultures were used. Cells were trypsinised with 0.25% trypsin; rinsed three times in serum free Eagle's medium. 4 ml aliquots of $5 \times 10^5$ cells in serum free medium (pH 7.2–7.4) were inoculated in each chamber and incubated at 34° C. At different intervals, the multiplates were subjected to gyratory shaking for 3 minutes in a shaker at 220 rpm; the weakly attached and floating cells were drained; the coverslips were rinsed in saline and fixed in 2% glutaraldehyde in saline.

The coverslips were examined in the microscope and cells were counted in 8 different randomly selected areas and the mean number of cells per unit were calculated. The number of cells adhered as a function of time is shown in FIG. 1.

The data indicates that the number of cells attached to 3,3-ionene treated coverglass is greater than that of untreated coverglass. This would probably mean that more adhesive sites are established in the presence of the polycation coating increasing the strength of adhesion within the given time.

Figure 2:
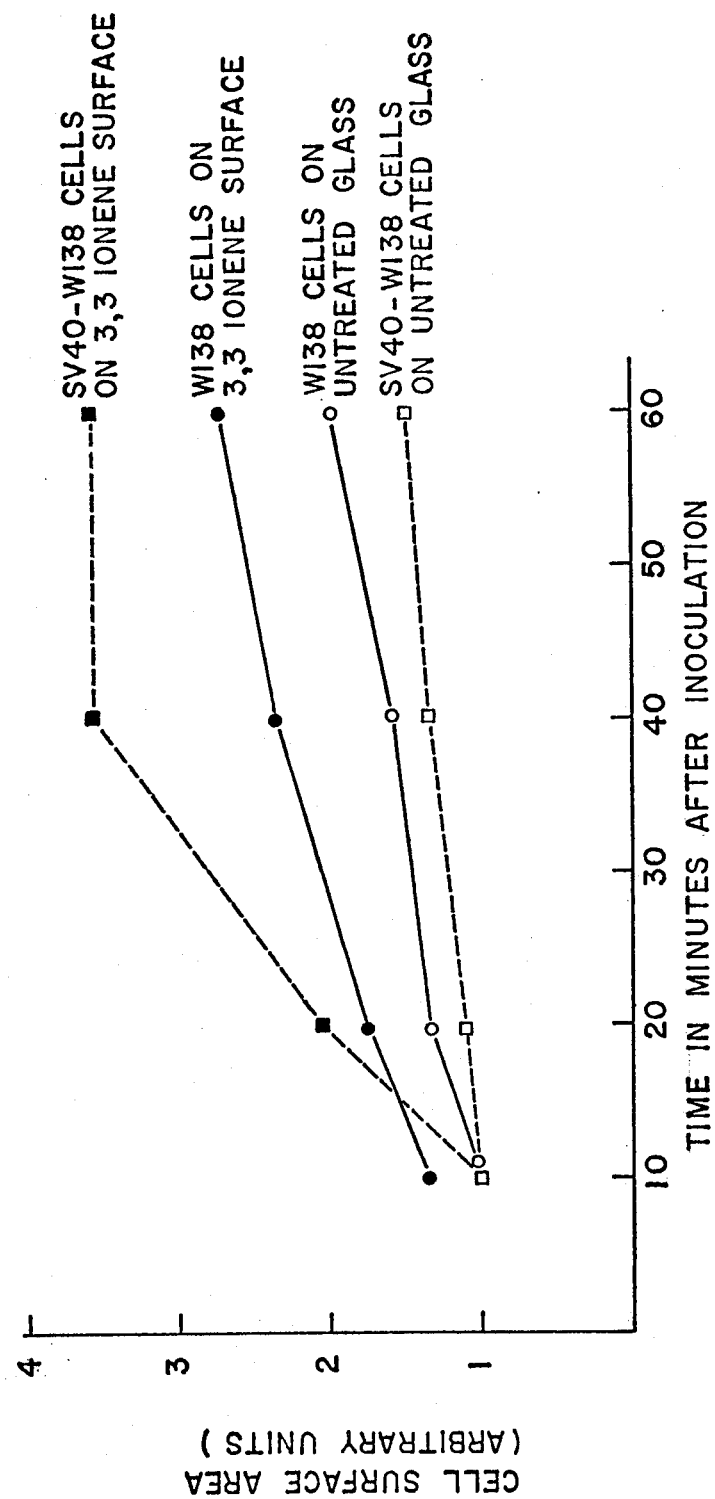
FIG. 2 is a series of curves showing the cell adhesion area on glass surfaces and on ionene-treated glass surfaces.

Cell flattening or cell spreading was also accelerated in both normal and transformed WI-38 cells. This was studied by randomly selected photographs (uniform magnification) of cell samples, carefully marking the cell boundaries and cutting the photographs along the boundary and weighing a total of 30-40 cells/treatment at different times. The area of a cell on the glass is shown in arbitrary units in the following table and plotted in FIG. 2 as a function of time. This data has the limitations of light microscope resolution.

Table 2

Area occupied by a cell on the glass surface in arbitrary units. (Each number is an average of 30-40 cells)

|  | 10 min. | 20 min. | 40 min. | 60 min. |
|---|---|---|---|---|
| WI-38 cells on untreated glass | 1.0 | 1.3 | 1.6 | 2.0 |
| WI-38 cells on 3,3-ionene surface | 1.3 | 1.7 | 2.3 | 2.7 |
| SV-40-WI-38 cells on untreated glass | 1.0 | 1.1 | 1.3 | 1.4 |
| SV-40-WI-38 cells on 3,3-ionene surface | 1.0 | 2.0 | 3.5 | 3.5 |

There is an acceleration in cell spreading in both normal and transformed WI-38 cells in the presence of 3,3-ionene coating, which is markedly pronounced in the SV-40 transformed WI-38 cells.

This is compatible with the assumption that polycation coated glass surfaces have more positive charges and the high negativity of the transformed cell membrane. One experiment was conducted with SV-40 transformed 3TC cells (Balb c mouse). These also showed a marked increase in cell spreading on the polyionene treated glass surface.

Figure 3:
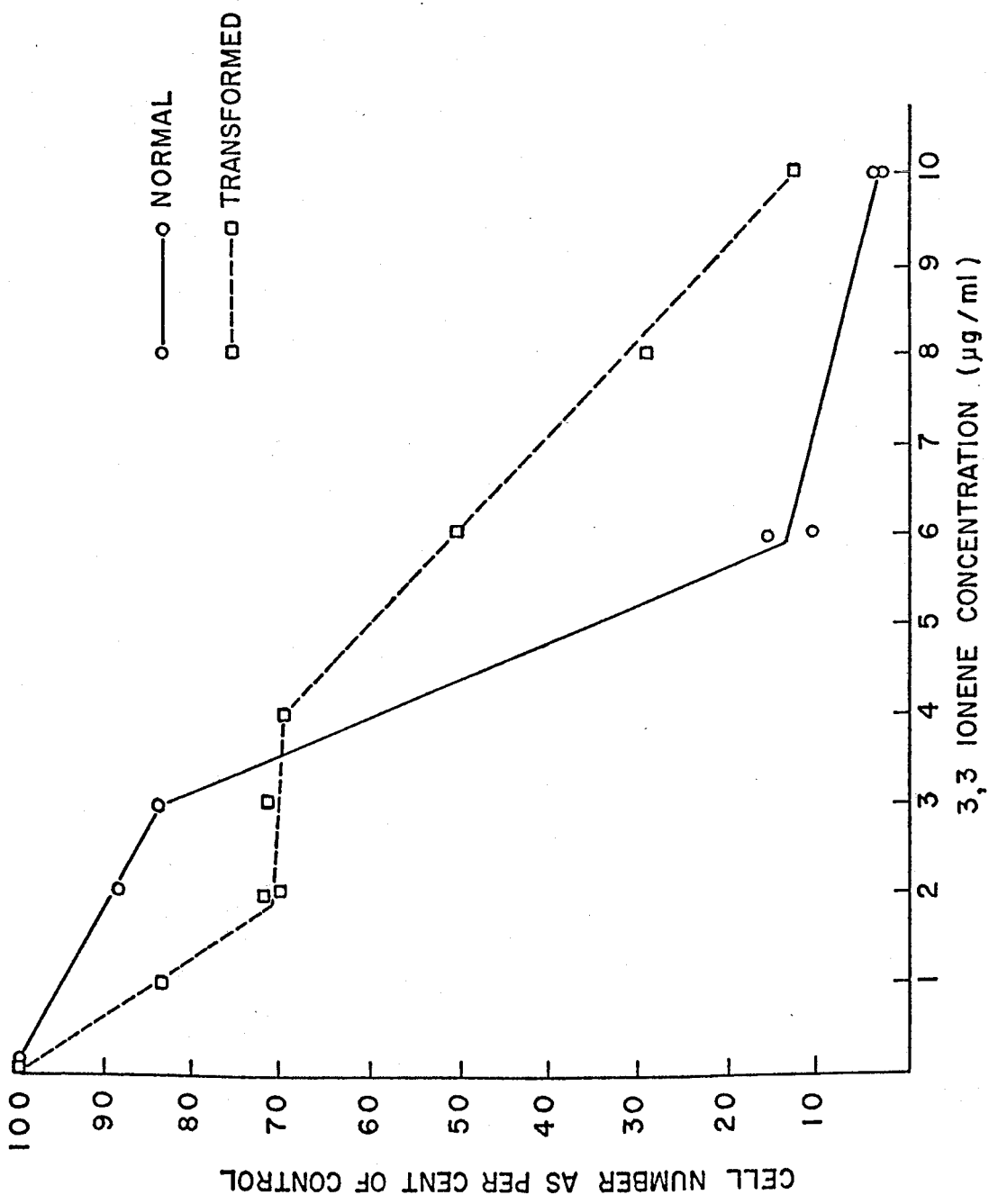
FIG. 3 is a pair of curves showing the toxic effect of 3,3-ionene on a mixture of normal and malignant cells.
Figure 4:
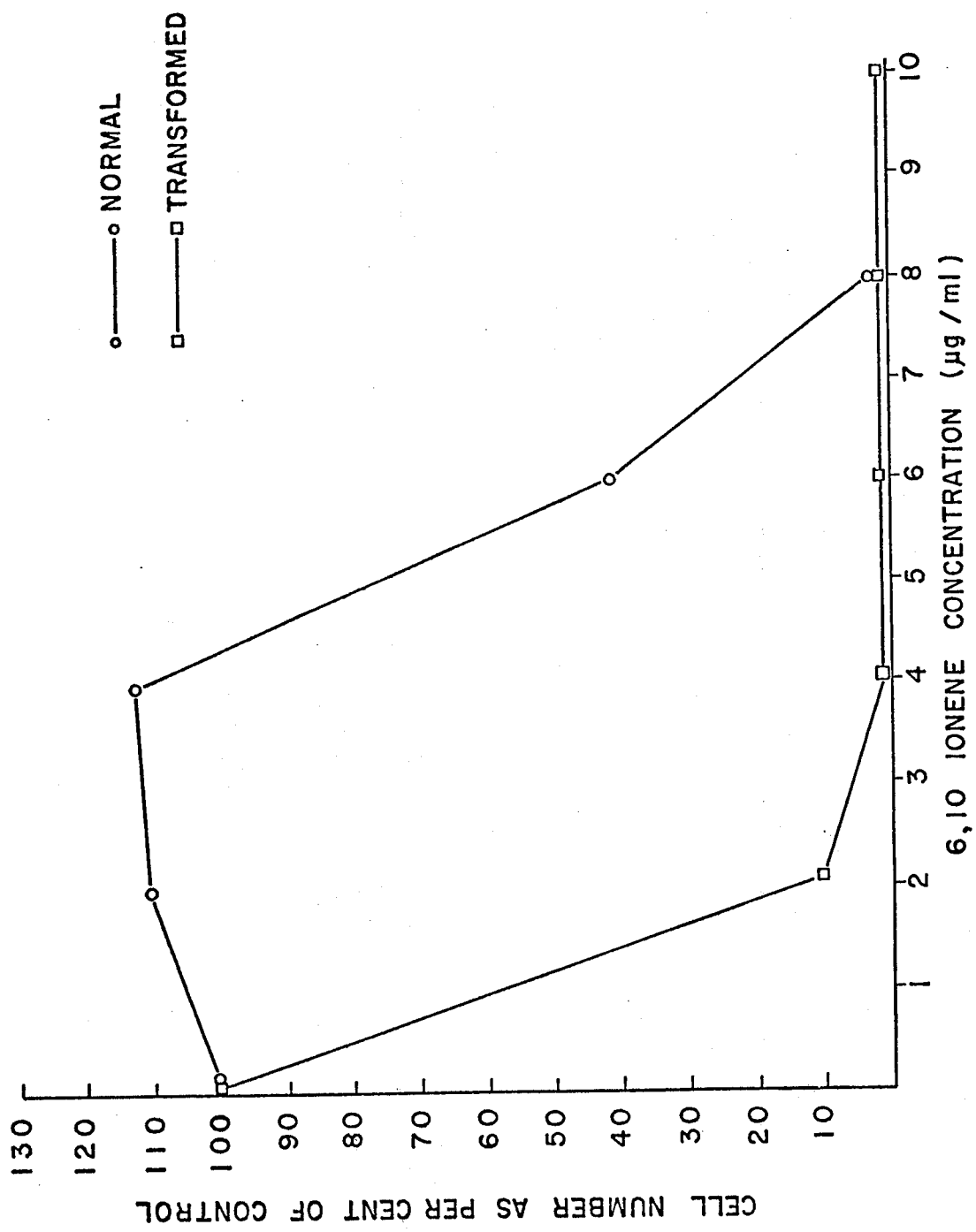
FIG. 4 is a pair of curves showing the toxic effect of 6,10-ionene on a mixture of normal and malignant cells.

Differential toxicity studies were conducted by Coulter counter analysis of WI-38 and SV-40 transformed cells in suspension in Eagle's medium treated with various concentrations of 3,3-ionene Br and 6,10-ionene Br and incubated for three days at room temperature. 3,3-ionene showed only moderate differences in the growth and survival rates of the two cell types as shown in FIG. 3. 6,10-ionene bromide showed highly specific toxicity to cancer cells, while the normal cells showed a slight stimulatory response with up to 4 µg/ml concentration of 6,10-ionene Br as shown in FIG. 4. The exact mechanism of specific toxicity to transformed cells is not known. It is probable that electrokinetic binding of the ionene to the negatively charged surface causes charge neutralization and cytotoxic reaction. The toxic activity may also result from pinocytosis by polycations binding to the cell nuclei.

It appears that the lower charge distribution and pattern of repeating intramolecular charge centers in the 6,10-ionene polymer backbone is surprisingly more toxic to cells than the higher charge distribution in 3,3-ionene polymer. These studies have shown that cell adhesion and spreading on glass surface is accelerated by the presence of polycation coating and shows a differential interaction with the transformed cells due to higher electronegativity. The charge distribution in the ionene polymer chain may provide higher specificity for malignant cells. The different degrees of ionene binding of the cells to surfaces also indicates a differential toxicity toward normal and malignant cells.

Though the mechanism of ionene cell interaction is not completely understood, pretreatment of the cells with N-ethylmaleimide (NEM) inhibited cell adhesion on an ionene-coated surface and indicated the involvement of sulfhydryl groups on the cell periphery in the process of cell adhesion. Chemical interaction with DNA is also a possibility. In fact, ionenes form strong waterinsoluble complexes with DNA.

An aqueous solution of calf thymus DNA (Na content of 5.9%) when mixed with an aqueous solution of 6,10-ionene bromide (Br content 33.9%) results in a solid fibrous precipitate which when dry contains only 0.03% of Na and 0.2% of Br. The complex can be obtained in the form of fibers exhibiting strong birefringence in a polarizing microscope, and this implies that the helical configuration of DNA was preserved. The elemental analysis results indicate electrostatic bonding between the negative oxygen of the DNA phosphate groups and the positive nitrogens of the ionene and elimination of sodium bromide during complex formation. Although different structures of ionenes yield similar complexes, an examination of DNA molecular models shows that the 6,10-ionene gives the best fit if we assume that the latter wraps itself around the DNA double helix.

The ionene-DNA complex is soluble in high inonic strength solutions (0.5 M NaCl) but its stability has not yet been determined. Similar complexes have been obtained with polyamines of the following structures:

Spermidine

Spermine

Putrescine

These polyamines, in spite of the fact that they exhibit high toxicity when injected in vivo, are present in most living organisms and affect a large number of metabolic transformations. Spermine was discovered in the human semen as long ago as 1678 by Leeuwenhoek. It is now known that spermidine and spermine and the related diamine, putrescine, are ubiquitous in animals and plants and at least one of these three amines is present in all micro-organisms. Spermidine and spermine bind to DNA and may be attached like the histones along sections of a DNA molecule. Polyamines also have a marked stimulatory effect on the enzyme synthesizing ribonucleic acid (RNA) that is DNA primed RNA polymerase. They also stimulate the DNA replicating enzyme (DNA -primed DNA polymerase) and may stabilize the low molecular weight RNA (transfer RNA). The polyamines interact also with ribosomes, the subcellular particles which are functional in protein synthesis.

Since at pH 7 the polyamines exist in the form of polycations, their binding to DNA probably involves the same mechanism as proposed for ionene-DNA complexes. The 3,4-ionene can therefore be considered as a model for polyspermidine or polyspermine and since the molecular weight of ionenes and the number of positively charged nitrogens can be made considerably higher than in naturally occurring polyamines, the number of electrostatic bonds between DNA and ionenes is necessarily higher, therefore the resulting complexes should be more stable. It must be, however, borne in mind that the 3,4-ionene, in contrast to Spermine, does not contain hydrogen atoms capable of hydrogen bonding with oxygens of the phosphate groups and this fact may affect the stability of its complexes with nucleic acids or its biological activity.

In vivo experiments were conducted by inoculating Type C3H mice with 7 × 10⁵ of Type C3H/BA adenocarcinoma cells. When the mice were in terminal condition, groups of four mice were injected daily by i.p. with a daily dose of ionene in phosphate buffer at pH 7. Ten control animals received no treatment. The results are summarized in the following table.

Table 4

| Ionene Polymer | Number of Mice | Daily Ionene Dose for 30 days mg/kg | Percent of Mice That Rejected Tumor |
|---|---|---|---|
| None | 10 | — | 0 |
| 3,3-Bromide | 4 | 12.5 | 25 |
| 3,4-Bromide | 4 | 12.5 | 25 |
| 6,10-Bromide | 4 | 7.5 | 25 |

As can be seen, one of each animal in the treated group rejected the transplant. Two of the four mice administered 3,4-ionene bromide survived the last control by ten days. All the control animals developed tumors and died within 38 days. Of the ionenes tested, the 6,10-ionene bromide exhibited the strongest toxicity toward tumor cells. One cure was achieved when 3,3-ionene bromide was combined with a polyethyleneimine and injected into a mouse with transplanted tumor in terminal condition.

Two C3H type mice in terminal condition with adenocarcinoma from transplanted tumors (seven weeks old) were injected twice within 4 hours intraperitoneally with 500 μg of PC-6 (Example 7). A dramatic improvement was observed. Within one day the general health condition of the mice improved visibly and the diarrhea was stopped. The behavior of the mice continued normal for eleven days after injection. In another test, two B16 type mice with melanoma were similarly treated with equally encouraging results.

PC-6 differs from cyclophosphamide, a well-known clinically used antileukemia and antitumor drug, in its biological activity, toxicity and other properties. Nine doses of PC-6 of 100 mg/kg per day each were injected into 12 mice without visible ill effects as observed during this time. Similar doses of cyclophosphamide are lethal within a much shorter time.

Though the ionenes have been discussed and tested in their halide form, they may be converted to other anion forms for use. The ionene binding of electronegative cells will find use in clinical and diagnostic medicine. A diagnostic test for cancer can be practiced by culturing a tissue sample with 6,10-ionene bromide at a concentration of between 2-4 μg/ml and determining the presence of any dead cells in the culture since under these conditions normal cell growth is promoted while the ionene is toxic to malignant cells.

It is to be understood that only preferred embodiments of the invention have been described and that numerous substitutions, alterations and modifications may be made without departing from the spirit and scope of the invention as defined in the following claims.

What is claimed is:

1. A method of selectively inhibiting the in vitro growth of malignant animal cells comprising the steps of:
adding to a mixture of normal and malignant cells an ionene polymer in an amount sufficient to selectively inhibit the growth of said malignant cells, said polymer having a molecular weight from 3,000 to 100,000 of the formula:

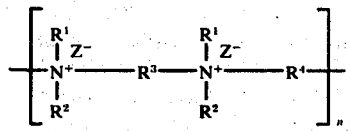

where $R^1$ and $R^2$ are lower alkyl, $R^3$ and $R^4$ are divalent aliphatic, aromatic or heterocyclic groups containing at least 3 carbon atoms, or $R^3$ combined with $R^1$ and $R^2$ forms a cyclic group, $Z^-$ is an anion and n is an integer; and
binding said polymer to said malignant cells.

2. A method according to claim 1 in which the cells are mammalian cells.

3. A method according to claim 2 in which the concentration of ionene polymer is no greater than 4 μg/ml.

4. A method according to claim 2 in which the ionene polymers have a molecular weight from 10,000 to 60,000.

5. A method according to claim 4 in which $R^3$ and $R^4$ are selected from alkylene, alkenylene, arylene, alkarylene and aralkylene.

6. A method according to claim 5 in which $R^3$ and $R^4$ are alkylene of 3-16 carbon atoms and $R^1$ and $R^2$ are methyl.

7. A method according to claim 6 in which $R^3$ is hexamethylene and $R^4$ is decamethylene.

8. A method according to claim 1 further including the step of coating the ionene polymer onto a surface and applying the cell mixture to the coated surface.

9. A method according to claim 8 in which the surface has a net negative charge before said coating is applied.

10. A method of determining the presence of malignant cells in a cell mixture comprising the steps of:
culturing said cells;
adding to said culture ionene polymer in an amount sufficient not to inhibit growth of normal cells and in an amount toxic to said malignant cells; said ionene polymer having a molecular weight from 3,000 to 100,000 of the formula:

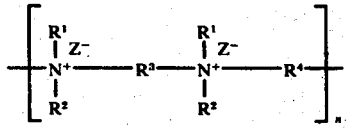

where $R^1$ and $R^2$ are lower alkyl, $R^3$ and $R^4$ are divalent aliphatic, aromatic or heterocyclic groups containing at least 3 carbon atoms, or $R^3$ combined with $R^1$ and $R^2$ forms a cyclic group, $Z^-$ is an anion and $n$ is an integer; and
determining the presence of dead malignant cells in the mixture.

11. A method according to claim 10 in which the ionene is a 6,10-ionene and the concentration is below 4 μg/ml.

12. A method according to claim 10 in which said cells are cultured on a surface having a net negative charge and further including the step of coating said surface with said ionene polymer.

13. A method according to claim 12 in which the surface is glass.

14. A method according to claim 13 in which a solution of ionene polymer is applied to the surface.

* * * * *